(12) United States Patent
Hallam et al.

(10) Patent No.: US 6,465,514 B1
(45) Date of Patent: *Oct. 15, 2002

(54) METHODS AND COMPOSITIONS FOR THE PROMOTION OF HAIR GROWTH

(76) Inventors: Kenneth M. Hallam, 9609 Labrador La., Cockeysville, MD (US) 21030; Howard N. Robinson, 18 Hickory Knoll Ct., Lutherville, MD (US) 21093

( * ) Notice: Subject to any disclaimer, the term of this patent is extended or adjusted under 35 U.S.C. 154(b) by 41 days.

This patent is subject to a terminal disclaimer.

(21) Appl. No.: 09/696,831

(22) Filed: Oct. 26, 2000

Related U.S. Application Data

(63) Continuation-in-part of application No. 08/608,954, filed on Feb. 29, 1996, now Pat. No. 6,187,815, which is a continuation-in-part of application No. 07/837,222, filed on Feb. 18, 1992, now abandoned, which is a continuation of application No. 07/013,772, filed on Jan. 12, 1987, now abandoned, which is a continuation-in-part of application No. 06/947,528, filed on Dec. 29, 1986, now abandoned.

(51) Int. Cl.⁷ .................. A61K 31/24; A61K 31/505; A61K 31/44; A61K 31/42
(52) U.S. Cl. .................. 514/535; 514/275; 514/356; 514/374
(58) Field of Search .................. 514/535, 275, 514/356, 256, 284, 374

(56) References Cited

U.S. PATENT DOCUMENTS

| | | | |
|---|---|---|---|
| 3,644,364 A | 2/1972 | Anthony | 260/256.4 H |
| 3,952,099 A | 4/1976 | Smith | 424/227 |
| 4,139,619 A | 2/1979 | Chidsey, III | 424/45 |
| 4,329,338 A | 5/1982 | Szegö et al. | 424/180 |
| 4,596,812 A | 6/1986 | Chidsey, III et al. | 514/256 |
| 5,182,269 A | 1/1993 | Gazzani | 514/44 |
| 5,215,760 A | 6/1993 | Kavoussi et al. | 424/680 |
| 5,480,889 A | 1/1996 | Goldman | 514/310 |
| 5,512,275 A | 4/1996 | Buck | 424/70.1 |
| 6,187,815 B1 * | 2/2001 | Hallam et al. | 514/535 |

OTHER PUBLICATIONS

Scholzel, 'Hair Growth in A 40–year old case of Alopecia After treatment with procaine', 1958, Medizinische Klinik, vol. 52, pp. 2239–2240, (English Translation).*
CAPLUS Abstract, AN 1967:31938, 1967, Serviere.*
CAPLUS Abstract, AN 1973:423508, 1973, Marttinen.*

* cited by examiner

Primary Examiner—Russell Travers
Assistant Examiner—Shengjun Wang
(74) Attorney, Agent, or Firm—Sam Rosen; Leonard Bloom

(57) ABSTRACT

Compositions, medicaments, and methods for the promotion of hair growth are disclosed. These compositions and medicaments are comprised of either local anesthetics of the secondary or tertiary amino type and/or niacin. The preferred secondary and tertiary amino compounds include those which are esters of para-aminobenzoic acid, esters of benzoic acid, esters of meta-amino benzoic acid, amides, ethers, and ketones. The preferred compositions and medicaments include either procaine hydrochloride or niacin or procaine hydrochloride and niacin in a non-sulfur-containing carrier. The disclosed compositions and medicaments may be topically applied to a scalp in need thereof by an eyedropper or other suitable means. An improved embodiment of this application adds minoxidil. Another improved embodiment administers Propecia™ orally while the anesthetic (e.g., procaine hydrochloride) and niacin are administered topically.

5 Claims, 1 Drawing Sheet

METHODS AND COMPOSITIONS FOR THE PROMOTION OF HAIR GROWTH

RELATED APPLICATIONS

The present application is a continuation-in-part of Ser. No. 08/608,954 filed Feb. 29, 1996 and now U.S. Pat. No. 6,187,815; which is a CIP of applicants' Ser. No. 07/837,222 filed Feb. 18, 1992, now abandoned; which is a CON of applicants' Ser. No. 07/013,772 filed Feb. 12, 1987, now abandoned; which is a CIP of applicants' Ser. No. 06/947,528 filed Dec. 29, 1986, now abandoned. The disclosures of these parent applications are herein incorporated by reference.

FIELD OF THE INVENTION

The present invention is directed to methods and compositions for promoting the activity of the hair follicles of a living organism and, in particular, to compositions, medicaments, and methods for the treatment of the hair follicles of a human scalp to promote the growth of hair thereon.

BACKGROUND OF THE INVENTION

At birth, the average human scalp has approximately 100,000-150,000 hair follicles. Initially, hair follicles normally exhibit fine lanugo hair shafts, which are commonly referred to as "baby hair". This lanugo hair "matures" eventually, into terminal hair shafts, which is the hair most often exhibited during adolescence and adulthood. Thereafter, this terminal hair may remain as such, or it may develop into non-terminal vellus hair, which is commonly referred to as a "thinning" of the hair and, in more advanced stages, baldness.

The precise mechanism that triggers the development of non-terminal vellus hair is not precisely understood or agreed upon. However, there have been numerous attempts to provide an effective safe prophylaxis to arrest development of non-terminal vellus hairs and even to stimulate the regeneration of these vellus hairs into terminal hair shafts. Unfortunately, none of these attempts have proven to be fully satisfactory.

Thus, it can be seen that there remains a need for compositions, medicaments, and methods for administering the same, which are effective in stimulating the development of terminal hairs from non-terminal vellus hairs, are safe for use with a human host, and which are easy to administer.

A patient's hair loss may be attributable to certain underlying symptomatic conditions or drug exposure, such as telogen effluvium and anagen effluvium. The compositions and methods of the invention may be employed to supplement or augment known treatments for such conditions.

To determine specific known causes of hair loss, a history is taken, and a physical examination is conducted. Once a known cause of hair loss is diagnosed for which a known treatment is accepted, then the known treatment can be instituted.

However, even with types of hair loss whose cause is determined and whose treatment is known, the rate of return of the lost hair may often be undesirably slow. It would be desirable, therefore, to be able to treat the patient being treated for a known cause of hair loss to accelerate the return of hair to such patients.

As further background, it is noted that some vasodilators have been tried topically to treat hair loss, and these vasodilators have not been effective. For example, diazoxide has been tried topically on the scalp to promote hair growth, but this was not deemed to be effective.

It would be desirable to provide effective topical treatments of the hair loss conditions for which satisfactory topical treatments are not currently available.

A number of patents and publications have been uncovered which may be relevant to the scalp treatment methods and compositions of the invention set forth herein below. These patents and publications are as follows, in approximate chronological order:

1. U.S. Pat. No. 4,139,619 of Chidsey (1979)
2. U.S. Pat. No. 4,329,338 of Szego et al (1982)
3. U.S. Pat. No. 4,596,812 of Chidsey et al (1986)
4. U.K. Patent Application No. 2 177 919A of Salim (1987)

More specifically, with respect to literature references, the following summaries of their disclosures are provided.

1. French patent no. 336,814 of Ascoli (1904) appears to disclose a composition used to promote hair growth. The composition appears to disclose the active ingredient to be the chlorhydrate of cocaine. The carrier appears to be a grease, such as vaseline, to form a pomade.
2. New York State Journal of Medicine, Vol. 49, (1949), pages 1317-1318, discloses a solution of niacin and procaine hydrochloride that is used for intravenous administration to treat a number of conditions listed in Table 1. The conditions listed include traumatic, degenerative, inflammatory, and miscellaneous conditions, none of which include hair loss. The composition was administered in an isotonic saline solution. There is a disclosure that niacin or nicotinic acid has a vasodilating effect, especially upon the capillary bed.
3. Aslan A, in Med. Klin.: 52, 758, 1759, 1760 (1957), appears to disclose, as indicated in the translation of the Scholzel article referred to below, that procaine has been used in injection or intravenous therapy of old people resulting to better mental and physical performance abilities, increase in muscle strength, improvement of rigidity, and stimulation of hair growth in many cases of baldness.
4. Scholzel, P., in Med. Klin.: 53, 2239 (1958), in an English translation of the article in German, discloses the general content of the Aslan article mentioned above and goes on to disclose findings relating to a specific patient who, after 40 years of alopecia, showed hair growth after intravenous procaine therapy. There is also a disclosure that a person named Kohler, reported in 1957, the use of a combination of procaine with various vitamins in an apparently injectable composition ("Gerioptil pro injectione"). However, the specific use of effects of the Kohler compositions were not disclosed.
5. French patent no. 1439833 of Serviere (1966) appears to disclose a composition which contains a synergistic combination of the following ingredients: malic acid, procaine, and a soluble derivative of sulfapyridine. The composition is apparently applied topically to improve hair characteristics, but not necessarily hair growth.
6. U.S. Pat. No. 3,644,364 of Anthony (1972) discloses a process for preparing compounds which include minoxidil, an agent that may promote hair growth.
7. Chemical Abstracts No. 79:23508s (1973) discloses an abstract of a German patent (to Indal Oy) that discloses hair growth promoting characteristics. The disclosures in the German patent of Indal Oy appear to be similar to the disclosures in French patent no. 72.39675 of Indal Oy (1973) and UK patent no. 1 354 446 of Indal Oy (1974) mentioned below.

8. French patent no. 72.39675 of Indal Oy (1973) appears to disclose the compositions that are disclosed in UK patent no. 1 354 446 of Indal Oy (1974).

9. UK Patent No. 1 354 446 of Indal Oy (1974) discloses a composition for promoting the growth of hair. The composition contains nicotinic acid and salicylic and/or benzoic acid dissolved in a carrier containing ethanol, urea, polyoxyethylene sorbitan-monopalmitate or monostearate, with the remainder being isopropyl myristate.

10. U.S. Pat. No. 3,952,099 of Smith (1976) is very similar in its disclosure to U.S. Pat. No. 3,896,238 to Smith (1975).

11. U.S. Pat. No. 4,139,619 of Chidsey (1979) discloses compositions which employ minoxidil in carriers to be applied topically to a scalp to promote hair growth.

12. UK Patent No. 1 603 639 of Haggar (1981) discloses a composition for application to the hair and scalp for use in stimulating hair growth in treating alopecia and excessive hair loss. The composition includes a hair conditioner (lotion or cream) and a vitamin solution which contains vitamins B1, B2, B2, A, D, nicotinamide, and ascorbic acid. It has been found particularly advantageous to use Oil of Rosemary in the vitamin solution. More specifically, in one preferred embodiment, Oil of Rosemary is included. In another preferred embodiment, Oil of Balsam is included. In addition, the carrier can be the conditioner LIFE-TEX (T.M.) produced by Wella, which has been found satisfactory. The carrier desirably promotes absorption into the scalp and is preferably an antiseptic type spirit which may be alcohol, isophane insulin, or other biologically acceptable volatile liquid. However, white iodine is the preferred carrier. Petroleum jelly or liquid paraffin may also be included. There is a statement that the composition for application to the hair and scalp includes a commercial hair conditioner and a vitamin solution which contains one or more of the disclosed vitamins.

13. U.S. Pat. No. 4,329,338 of Szego et al (1982) discloses compositions for use as cosmetics. The compositions include a reaction product of nicotinic acid, a nicotinic acid salt, or a nicotinic acid halide and a polyhyroxy compound whose general formula is given in the Abstract. The active agents are disclosed as exerting beneficial effects for stimulating scalp or hair bulbs.

14. U.S. Pat. No. 4,596,812 of Chidsey et al (1986) discloses methods and compositions for treating male pattern alopecia. The compositions include the substance known as minoxidil. Minoxidil is disclosed as a vasodilator that functions to dilate the peripheral vascular system. Minoxidil compositions are applied topically to the scalp and are used in a carrier system which can include equal parts of ethyl alcohol and propylene glycol.

15. UK patent application on. 2 176 104A of Grollier (1986) discloses compositions for the treatment of hair and of the scalp to promote fresh hair growth. It is disclosed that compositions containing nicotinic acid or its esters, when applied to the scalp, have rubefacient and vasodilant activity. The specific compositions disclosed in this patent include the combination of certain water-soluble polyamides of the poly-beta-alanine type with nicotinic acid or its esters. As shown in Examples 1 and 4, for a hair-care lotion, the carrier includes ethyl alcohol and water.

16. UK patent application on. 2 177 919A of Salim (1987) discloses, in Example 9, a topical preparation to restore hair growth to areas of the human scalp suffering from hair loss. The preparation includes procaine, a physiologically acceptable, organic, in vivo sulphydryl group releasing agent, and castor oil.

The following conclusions can be made from a consideration of the prior art discussed above. Procaine has been used topically, in the presence of other active ingredients and in the presence of complex carrier ingredients, often including sulfur-containing carriers, to treat the scalp for hair growth. It is also clear from the prior art that neither procaine nor niacin, either alone or in combination with one another, has been used topically without other active ingredients and without a complex carrier system which often includes sulfur-containing carriers and non-hydrophilic ingredients.

Carriers containing sulfur-containing ingredients have their problems. for example, the safety and efficacy of dimethylsulfoxide (DMSO) has not been sufficiently established for the U.S. Food and Drug Administration to permit its use in the United States.

Carriers containing non-hydrophilic ingredients may have the undesirable property of impeding or preventing penetration of the active, hair-bulb treating agents into the hair bulb from the surface of the skin when the active ingredient is applied topically.

SUMMARY OF THE INVENTION

Accordingly, it is a primary object of the present invention to alleviate the disadvantages and deficiencies of the prior at by providing compositions and medicaments that are effective for stimulating the development (growth) of terminal hairs from the hair bulb of non-terminal vellus hair follicles.

It is another primary object of the present invention to provide compositions and medicaments which may safely be used with a human host.

It is still another primary object of the present invention to provide methods for stimulating the development (growth) of terminal hairs from the hair bulb of non-terminal vellus hair follicles.

Another object of the present invention is to provide topical methods of treating scalp hair loss and to stimulate scalp hair growth by employing solutions containing simply procaine (or a derivative thereof) and/or niacin in a simple, water-miscible carrier.

Still another object of the invention is to provide a topically applied composition that includes an agent that will stimulate hair growth by stimulating the hair bulb and that also includes a non-sulfur-containing carrier.

Yet another object of the invention is to provide a topically applied composition that includes an agent that will stimulate hair growth by stimulating the hair bulb and that also contains a carrier that does not include a sulfur-containing ingredient.

Still another object of the invention is to provide a topically applied composition that includes an agent for stimulating hair growth by stimulating the hair bulb and that also contains a carrier that does not contain non-hydrophilic ingredients.

In accordance with the teachings of the present invention, there is disclosed the use of a secondary or tertiary amino local anesthetic for the manufacture of a topical medicament for stimulating the growth of a hair bulb of a vellus hair follicle.

Preferably, the secondary or tertiary amino local anesthetic is either a secondary or tertiary amino ester of para-aminobenzoic acid, or a secondary or tertiary amino type ester of either benzoic acid or meta-aminobenzoic acid, or a secondary or tertiary amino type amide or a secondary or tertiary amino type ether, or a secondary or tertiary amino type ketone.

In further accordance with the teachings of the present invention, there is disclosed the use of niacin for the manufacture of a topical medicament for stimulating the growth of a hair bulb of a vellus hair follicle.

In yet another aspect of the present invention, methods are disclosed for stimulating the growth of a hair bulb for a vellus hair follicle that involves the topical administration of a therapeutic amount of the medicaments described above to a patient in need thereof.

In still further accordance with the teachings of the present invention, a composition for stimulating the growth of a hair bulb of a vellus hair follicle is disclosed. This composition includes either a secondary or tertiary amino local anesthetic or niacin as its active ingredient. This composition further includes a pharmaceutically-acceptable carrier.

Preferably, the carrier is a hydrophilic carrier that does not have a sulfur-based ingredient and that may be chosen from the group consisting of propylene glycol, absolute alcohol, and isopropyl alcohol. Alternatively, a combination of two or more of these carriers may be employed.

In another aspect of the present invention, there is disclosed a method for stimulating the growth of a hair bulb of a vellus hair follicle. This method includes, first, preparing a composition for stimulating the growth of a hair bulb of a vellus hair follicle which includes either niacin or a secondary or tertiary amino local anesthetic as its active ingredient, and a hydrophilic carrier; and second, topically applying the composition to a scalp having a vellus hair follicle in need thereof

DETAILED DESCRIPTION OF THE PREFERRED EMBODIMENTS

Figure 1:
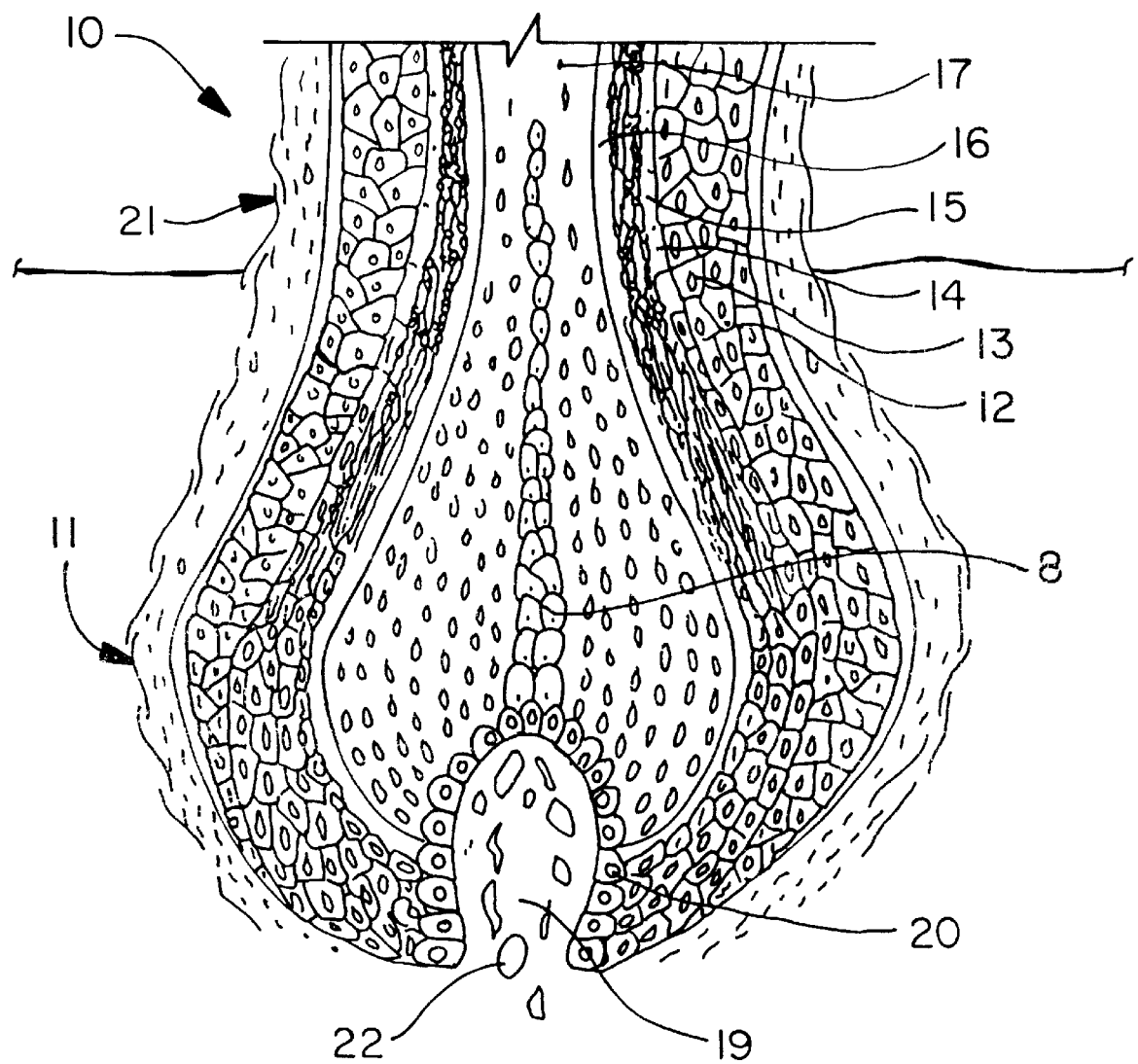
FIG. 1 illustrates, in cross-section, a healthy terminal hair follicle.

With reference now to FIG. 1, the hair follicle 10 includes a hair bulb 11 at the lower end thereof. The hair bulb 11 of the average mature hair follicle lies approximately 0.5–4 mm below the stratumcorneum of the epidermis.

Generally, and as referred to herein, the hair follicle is comprised of seven layers: the outer root sheath 12; Henle's layer 13; Huxley's layer 14; cuticle of inner root sheath 15; the cuticle of hair shaft 16; the cortex of hair shaft 17; and the medulla of hair shaft 8. Further as referred to herein, the base of the hair follicle comprises a hair bulb 11 which surrounds a dermal papilla 19. Above the dermal papilla 19 is a germative cellular layer 20 which is the active growth portion of the hair shaft 21.

The compositions and medicaments (therapeutic compounds) of the present invention utilize a powerful vasodilator, especially one having strong local effects, as an active ingredient. Also, a pharmaceutically-acceptable hydrophilic carrier, devoid of a sulfur-containing ingredient, is utilized as an adjunct. The preferred active ingredient is either a secondary or tertiary amino local anesthetic or niacin.

The preferred secondary or tertiary amino local anesthetics (active ingredient) are the esters of para-aminobenzoic acid which include chloroprocaine, buthethamine, naepaine, and proparacaine. Especially preferred is procaine (which is also an ester of para-aminobenzoic acid) in the form of procaine hydrochloride procaine HCl).

Alternatively, the preferred active ingredient may also be an amide including dibucaine, bupivacaine, lidocaine, mepivacaine, and prilocaine.

Other local anesthetics of the secondary or tertiary amino, type which have applicability in the present invention as an active ingredient area; esters of benzoic acid such as cocaine, piperocaine, hexylcaine, meprylcaine, benoxinate, propoxycaine, and tetracaine; esters of meta-aminobenzoic acid, such as metabutethamine, isobucaine, and cyclomethycaine; ethers such as pramoxine and dimethisoquin; the ketone dyclonine; and the phenetidin derivative phenacaine.

Anesthetics which are esters of para-aminobenzoic acid that lack the terminal tertiary or secondary groups such as benzocaine (anesthesin), butyl aminobenzoate and orthoform would be operative for use in this invention.

If desired, niacin may also be added to the active ingredient enumerated above.

The preferred pharmaceutically-acceptable carrier of the compositions and medicaments of the present invention is propylene glycol. While not preferred, other carriers such as absolute alcohol (99% ethyl alcohol), and isopropyl alcohol may be employed either alternatively, or in combination therewith. Indeed, preferred compositions and medicaments are comprised of from 50% to 95% of propylene glycol and 15% to 30% of absolute alcohol. Other hydrophilic solutions, ointments, creams, and gels may also be employed.

One of the preferred compositions and medicaments useful in this practice is comprised of from 0.1–5% by weight of procaine hydrochloride (with 2% being preferred) in a carrier solution comprised of 50% to 95% by volume of propylene glycol (with 80% being preferred), 0.5 to 30% by volume ethyl (absolute) alcohol and 0.5 to 20% by volume of water (with 10% being preferred). These compositions and medicaments may be 0.1–5% by weight (with 2% being preferred) of procaine hydrochloride in carrier "vehicle N". Vehicle N is known as "Neutrogena Vehicle N" made by Neutrogena Dermatologics Division of Neutrogena Corporation, out of Los Angeles, Calif. 90045. Vehicle N as defined herein is a composition comprised of 47.5% by weight of ethyl alcohol, 4% by weight of isopropyl alcohol, 44% by weight of purified water, 0.5% by weight of Laureth-4 (a surfactant) and 4% by weight of propylene glycol.

It is possible that procaine is vasodilator that can have a prolonged action on hair bulbs. The procaine may be able to be applied only once a day because of its prolonged vasodilatory effects.

Variations of "vehicle N" that can be employed are as follows:

ethyl alcohol (in a range spanning 44.5%–51.0% by weight),

Laureth (in a range spanning 0.15–2.0% by weight), propylene glycol (in a range spanning 2.0%–6.0% by weight), isopropyl alcohol (in a range spanning 2.0%–6.0% by weight), and purified water (in a range spanning 40.0%–48.0% by weight).

It is noted that Laureth, which may be Laureth-4, is a surfactant. Alternate pharmaceutically-acceptable surfactants include ammonium lauryl sulfate, sodium lauryl sulfate, ammonium laureth sulfate, sodium myristate, sodium palmitate, among other pharmaceutically-acceptable surfactants.

Yet another preferred carrier is known as "Neutrogena Vehicle N (mild)" made by Neutrogena Dermatologics Division of Neutrogena Corporation, Los Angeles, Calif. 90045. This carrier approximately contains 41.5% by weight of ethyl alcohol, 6.0% by weight of isopropyl alcohol, 52.0% by weight of purified water, and 0.5% by weight of Laureth-4 (a surfactant).

Variations of "Vehicle N (mild)" that can be employed are as follows:

ethyl alcohol (in a range spanning 39.5%–43.50% by weight),

Laureth (in a range spanning 0.15–2.0% by weight), isopropyl alcohol (in a range spanning 47.0%–53.0% by weight), and purified water (in a range spanning 47.0%–53.0% by weight).

It is noted that Laureth, which may be Laureth-4, is a surfactant. Alternate pharmaceutically-acceptable surfactants include ammonium lauryl sulfate, sodium lauryl sulfate, ammonium laureth sulfate, sodium myristate, sodium palmitate, among pharmaceutically-acceptable surfactants.

If desired, niacin may also be added to the compositions and medicaments noted above. While the amount of niacin to be added may range from 0.01–5% by weight of the total composition or medicament, 0.1% is the preferred quantity.

Another of the preferred compositions and medicaments useful in this practice is comprised of a 0.01–5% by weight solution of niacin (with 0.1% being preferred) in a carrier solution comprised of 50 to 95% by volume of propylene glycol (with 80% being preferred), 0.5 to 30% by volume of ethyl (absolute) alcohol, and 0.5 to 20% by volume of water (with 10% being preferred). These compositions and medicaments may be comprised of from 0.01–5% (with 0.1% being preferred) of niacin in "vehicle N". Vehicle N as defined herein is a composition comprised of 47.5% by weight of ethyl alcohol, 4% by weight of isopropyl alcohol, 44% by weight of purified water, 0.5% by weight of Laureth-4 (a surfactant), and 4% by weight of propylene glycol.

The amount of niacin of the compositions and medicaments described above may range from 0.01–5% by weight of the total composition or medicament, with 0.1% of niacin being the preferred quantity.

These compositions and medicaments are topically applied directly to a scalp in need thereof by use of a dropper, a porous applicator, a roll top, small brush, or even by massaging in with the hands or any other means which is suitable for topical application which are well known to those skilled in the art. When a porous applicator is used, a microporous applicator is preferred, such as that provided in the package of Neutrogena Vehicle N, made by Neutrogena Dermatologics Division of Neutrogena Corporation, Los Angeles, Calif. 90045. The porous or microporous applicator is a filter designed to provide a controlled release of the drug to the surface of the skin. This filter utilizes a fine or ultra-fine porosity delivery system to provide a controlled release of the drug.

The precise amount of the compositions and medicaments to be applied is within the skill of the art to determine. However, the amount applied would be that quantity necessary to thinly saturate the affected area of the skin. In this regard, the application of from 1 to 3 cc of the compositions or medicaments will be preferable. These topical applications are preferably performed one to two times daily. the frequency of these applications may be increased to decreased, as needed, as would be obvious to one skilled in the art.

If desired, the compositions and medicaments may be incorporated in a shampoo or a gel form. In a shampoo, the compositions and medicaments include water, lauryl sulfate, a surfactant and, if desired, a fragrance. The shampoo is shaken prior to use to effect thorough mixing thereof and is hand-massaged into the scalp.

Compositions employed in carrying out the method of the invention will be more clearly perceived and better understood from the following specific examples.

In each example, unless otherwise indicated, the proportions presented for the active ingredients, such as niacin or procaine HCl, are on a weight % of active ingredient per unit volume of carrier ingredient basis (i.e., 5% procaine hydrochloride is 5 grams of procaine HCl per 100 cc of a pharmaceutically-acceptable topical carrier), and the proportions presented for the carrier consist of a percent by volume (i.e., 80% propylene glycol is 80 cc of propylene glycol per 100 cc of a pharmaceutically-acceptable topical carrier).

EXAMPLE ONE

A 2% solution of procaine hydrochloride in a propylene glycol carrier is prepared. Approximately 1 to 3 cc of this composition or medicament is then placed in an eyedropper. The composition or medicament is then administered in a dropwise fashion on a portion of a human scalp in need thereof. Initially, these applications are made every twelve hours. Eventually, the frequency of these applications may thereafter be decreased (or increased) as needed.

EXAMPLE TWO

A 0.1% solution of niacin in a propylene glycol carrier is prepared. Approximately 1 to 3 cc of this composition or medicament is then placed in an eyedropper. The composition or medicament is then administered in a dropwise fashion on a portion of a human scalp in need thereof. Initially, these applications are made every twelve hours. Eventually, the frequency of these applications may thereafter be decreased (or increased) as needed.

EXAMPLE THREE

A 2% solution of procaine hydrochloride in a carrier solution of 50% to 95% propylene glycol and 15% to 30% of absolute alcohol is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

EXAMPLE FOUR

A 0.1% solution of niacin in a carrier solution of 50% to 95% propylene glycol and 15% to 30% of absolute alcohol is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually, the frequency of these applications may thereafter be decreased (or increased) as needed.

EXAMPLE FIVE

A 2% by weight solution of procaine hydrochloride in a carrier solution of 47.5% by weight of ethyl alcohol, 4% by weight of isopropyl alcohol, 44% by weight purified water, 0.5% by weight of Laureth-4 (a surfactant) and 4% by weight of propylene glycol is prepared.

EXAMPLE SIX

A 0.1% by weight solution of niacin in a carrier solution of 47.5% by weight of ethyl alcohol, 4% by weight of isopropyl alcohol, 44% by weight of purified water, 0.5% by weight of Laureth-4 (a surfactant) and 4% by weight of propylene glycol is prepared.

EXAMPLE SEVEN

A 2% solution of procaine hydrochloride in a carrier solution of 80% propylene glycol, 10% water and 10% ethyl (absolute) alcohol is prepared.

EXAMPLE EIGHT

A 0.1% solution of niacin in a carrier solution of 80% propylene glycol, 10% water and 10% ethyl (absolute) alcohol is prepared.

EXAMPLE NINE

A 2% solution of procaine hydrochloride and 0.1% niacin in a propylene glycol carrier is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually the frequency of these applications may thereafter be decreased (or increased) as needed.

EXAMPLE TEN

A 2% solution of procaine hydrochloride in a propylene glycol carrier is prepared. Approximately 1 to 3 cc of this composition or medicament is placed in a container having a microporous applicator.

EXAMPLE ELEVEN

A 0.1% solution of niacin in a propylene glycol carrier is prepared.

EXAMPLE TWELVE

A 2% solution of procaine hydrochloride in a carrier solution of 50% to 95% propylene glycol and 15% to 10% of absolute alcohol is prepared.

EXAMPLE THIRTEEN

A 0.1% solution of niacin in a carrier solution of 50% to 95% propylene glycol and 15% to 30% of absolute alcohol is prepared.

EXAMPLE FOURTEEN

A 2% solution of procaine hydrochloride in a carrier solution of 80% propylene glycol, 10% water and 10% ethyl (absolute) alcohol is prepared.

EXAMPLE FIFTEEN

A 0.1% solution of niacin in a carrier solution of 80% propylene glycol, 10% water and 10% ethyl (absolute) alcohol is prepared.

EXAMPLE SIXTEEN

A 2% solution of procaine hydrochloride and 0.1% niacin in a propylene glycol carrier is prepared.

EXAMPLE SEVENTEEN

A solution of 0.1% niacin and 2% procaine hydrochloride in a carrier solution of 50% to 95% propylene glycol and 15% to 30% of absolute alcohol is prepared.

EXAMPLE EIGHTEEN

A solution of 0.1% by weight of niacin and 2% by weight of procaine hydrochloride in a carrier solution of 47.5% by weight of ethyl alcohol, 4% by weight of isopropyl alcohol, 44% by weight of purified water, 0.5% Laureth-4 (a surfactant) and 4% by weight of propylene glycol is prepared.

EXAMPLE NINETEEN

A solution of 0.1% niacin and 2% procaine hydrochloride in a carrier solution of 80% propylene glycol, 10% water, and 10% ethyl (absolute) alcohol is prepared.

EXAMPLE TWENTY

A solution of 0.1% niacin and 2% procaine hydrochloride in a carrier solution of 50% to 95% propylene glycol and 15% to 30% of absolute alcohol is prepared.

EXAMPLE TWENTY-ONE

A solution of 0.1% niacin and 2% procaine hydrochloride in a carrier solution of 47.5% by weight of ethyl alcohol, 4% by weight of isopropyl alcohol, 44% by weight of purified water, 0.5% by weight of laureth-4 (a surfactant), and 4% by weight of propylene glycol is prepared.

EXAMPLE TWENTY-TWO

A solution of 0.1% niacin and 2% procaine hydrochloride in a carrier solution of 80% propylene glycol, 10% water, and 10% ethyl (absolute) alcohol is prepared.

EXAMPLE TWENTY-THREE

A 0.1% by weight solution of niacin in a carrier solution of 41.5% by weight of ethyl alcohol, 6.0% by weight of isopropyl alcohol, 51.9% by weight of purified water, and 0.5% by weight of Laureth-4 (a surfactant), is prepared.

EXAMPLE TWENTY-FOUR

A solution of 0.1% by weight of niacin and 2.0% by weight of procaine hydrochloride in a carrier solution of 41.5% by weight of ethyl alcohol, 6.0% by weight of isopropyl alcohol, 49.9% by weight of purified water, and 0.5% by weight of Laureth-4 (a surfactant), is prepared.

The procaine-niacin hair growth composition has been clinically tested. The testing was done at the Johns Hopkins Medical Institution. Extensive testing was done and the results have been recorded in applicant's parent application Ser. No. 08/608,954. When the tests set forth in said parent application are viewed in their entirety, those skilled in the art can conclude that positive results have been obtained.

In a unique embodiment of this invention minoxidil can be incorporated into the hair growth stimulating composition of procaine and niacin. Rogaine® is a hair growth proprietary product containing minoxidil and manufactured by the Upjohn Company. Rogaine® contains 20 or 50 mg of minoxidil per milliliter in an alcohol base (a 2% or 5% solution). In use Rogaine is applied to the scalp in one milliliter dosages twice daily. Rogaine® can be applied by the use of a metered spray, extender spray or rub-on applicator, the dosage being for example, 20 mg of minoxidil in one milliliter of dosage solution. A 5% solution of Rogaine is approved by the F.D.A. for men, while a 2% solution is approved for women.

The final concentration of minoxidil added to the procaine and niacin composition would be 2% to 5%. An exemplary composition would contain 2% minoxidil or 5% minoxidil with 5% being preferred; a dosage concentration of 0.1–5% of procaine would be operative, with 5% being preferred; and the dosage range for niacin being 0.01–5%, with 0.1% being preferred. Vehicles containing acceptable surfactants (e.g., Laureth-4 and sodium lauryl sulfate), propylene glycol, ethyl alcohol and water could be used as solvent vehicles of the minoxidil, procaine and niacin composition.

The optimum concentration of minoxidil added to procaine and niacin composition of this invention would be 20 mg/ml or 50 mg/ml of final mixture (2% or 5%) of minoxidil. However, a final effective dosage of 1–5% minoxidil could be increased or decreased based on observed effect on hair growth.

Examples of compositions containing procaine, niacin and minoxidil:

EXAMPLE A

A solution of 0.1% niacin, 2% procaine hydrochloride and minoxidil 2% in a carrier solution of 50% to 95% propylene glycol and 15% to 30% of absolute alcohol is prepared. Approximately 1 cc of this composition or medicament is then placed in an eyedropper. The composition of medicament is then administered in a dropwise fashion to a portion of a human scalp in need thereof. Initially, the applications are made once every twelve hours. Eventually, the frequency of these applications may thereafter be decreased (or increased) as needed.

EXAMPLE B

A solution of 0.1% by weight of niacin and 2% by weight of procaine hydrochloride and 2% by weight of minoxidil in a carrier solution of 47.5% by weight of ethyl alcohol, 4% by weight of isopropyl alcohol, 44% by weight of purified water, 0.5% Laureth-4 (a surfactant) and 4% by weight of propylene glycol is prepared. Approximately 1 cc of this composition or medicament is then placed in an eyedropper. The composition or medicament is then administered in a dropwise fashion to a portion of a human scalp in need thereof. Initially, the applications are made once every twelve hours. Eventually, the frequency of these applications may thereafter be decreased (or increased) as needed.

In Examples A and B the percent of minoxidil can be raised to 5%.

The herein disclosed invention envisions procaine hydrochloride and niacin to be used together with Propecia™. Propecia™ 1 mg (Finasteride) is manufactured by Merck and Co. for use in treating male pattern hair loss. Propecia™ is an oral agent that blocks the enzyme 5-alpha reductase and can cause increase in the diameter of the hair shaft as well as hair growth. The medication is taken orally once a day.

In using Propecia™ with the compositions of this invention, the Propecia™ will be administered orally and the anesthetic (e.g., procaine hydrochloride and niacin will be applied topically. For example, a dosage of 1 mg of Propecia™ will be administered orally while 0.1-5% procaine hydrochloride and 0.01-5% niacin will be administered topically.

Propecia (finasteride) is a 4-azasteroid of the formula 4-azaandrost-1-ene-17-carboxamide, N-(1,1-dimethylethyl)-3-oxo-, (5α,17β)- and is set forth as such in the Physicians' Desk Reference.

The herein disclosed invention can be used on animals such as mink to promote fur (hair) growth.

The dosages herein set forth are optimum ranges, however, they may be increased or decreased based upon observed results by those skilled in the art.

An added benefit of an anesthetic, niacin and minoxidil composition is that this formulation besides enhancing hair growth, will mitigate certain side-effects produced by the use of minoxidil alone. The medical literature informs that minoxidil can cause itching of the scalp, and skin irritation. Adding a topically effective anesthetic to the minoxidil containing composition is intended to eliminate itching of the scalp and skin irritation which might be caused by the minoxidil.

Furthermore, obvious modifications or variations of the method of the invention are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended thereto. The expression "effective amount" is exemplified by the amounts set forth throughout the disclosure.

What is claimed is:

1. A method for stimulating hair growth on the scalp by topically applying to the scalp, effective amounts of a topical composition consisting essentially of 0.1–5% procaine hydrochloride, 0.01–5% niacin and 1–5% minoxidil in a topical hydrophilic vehicle for said procaine hydrochloride, niacin and minoxidil.

2. A topical composition for stimulating hair growth on the scalp, the composition consisting essentially of a combination of niacin, procaine hydrochloride and minoxidil in a pharmaceutically acceptable carrier containing propylene glycol for penetrating the scalp and for carrying the niacin, procaine hydrochloride and minoxidil therewith.

3. The composition of claim 2, wherein the niacin ranges from 0.01 to 5% of the total composition, the amount of procaine hydrochloride ranges from 0.1 to 5% of the total composition and the amount of minoxidil ranges from 1–5% of the total composition.

4. The composition of claim 2, wherein the pharmaceutically acceptable carrier further includes a carrier chosen among the group consisting of lanolin, butyl alcohol, absolute alcohol, isopropyl alcohol and dimethyl sulfoxide, or a combination of two or more of these carriers.

5. A method for stimulating hair growth on the scalp by topically applying to the scalp, effective amounts of a topical composition consisting essentially of 0.1–5% procaine hydrochloride and niacin; and orally administering 1 mg dosage of 4-azaandrost-1-ene-17-carboxamide, N-(1,1-dimethylethyl)-3-oxo-, (5α,17β)-.

\* \* \* \* \*